(12) United States Patent
Li et al.

(10) Patent No.: US 9,058,658 B2
(45) Date of Patent: Jun. 16, 2015

(54) METHODS AND DEVICES FOR LOCATING OBJECT IN CT IMAGING

(71) Applicants: Tsinghua University, Beijing (CN); Nuctech Company Limited, Beijing (CN)

(72) Inventors: Liang Li, Beijing (CN); Li Zhang, Beijing (CN); Zhiqiang Chen, Beijing (CN); Ziran Zhao, Beijing (CN); Yuxiang Xing, Beijing (CN); Yongshun Xiao, Beijing (CN); Qingli Wang, Beijing (CN)

(73) Assignees: Tsinghua University, Beijing (CN); Nuctech Company Limited, Beijing (CN)

( * ) Notice: Subject to any disclaimer, the term of this patent is extended or adjusted under 35 U.S.C. 154(b) by 84 days.

(21) Appl. No.: 14/037,236

(22) Filed: Sep. 25, 2013

(65) Prior Publication Data

US 2014/0093152 A1    Apr. 3, 2014

(30) Foreign Application Priority Data

Sep. 29, 2012    (CN) .......................... 2012 1 0375312

(51) Int. Cl.
*A61B 6/00*   (2006.01)
*G06T 7/00*   (2006.01)
*G06T 11/00*   (2006.01)
*G06F 19/00*   (2011.01)

(52) U.S. Cl.
CPC ........... *G06T 7/004* (2013.01); *G06T 2211/421* (2013.01); *A61B 6/466* (2013.01); *G06F 19/3406* (2013.01); *A61B 6/4085* (2013.01); *A61B 6/469* (2013.01); *G06T 7/0065* (2013.01); *G06T 11/006* (2013.01); *G06T 2211/436* (2013.01); *G06T 7/0012* (2013.01)

(58) Field of Classification Search
CPC ...... A61B 6/4085; A61B 6/469; A61B 6/466; G06T 2211/421; G06F 19/3406
See application file for complete search history.

(56) References Cited

U.S. PATENT DOCUMENTS

2003/0202637 A1* 10/2003 Yang .............................. 378/210
2008/0232540 A1*  9/2008 Yoshimura et al. ............... 378/4

* cited by examiner

*Primary Examiner* — Amir Alavi
*Assistant Examiner* — Kenny Cese
(74) *Attorney, Agent, or Firm* — Knobbe, Martens, Olson & Bear, LLP

(57) ABSTRACT

The present disclosure provides methods and devices for locating a plurality of interested objects in CT imaging. Location of the interested objects in the three-dimensional space can be determined by using three projection images that are substantially perpendicular to each other. The method can rapidly locate interested objects in a CT image without pre-reconstruction of the CT image even if there are a plurality of interested objects in the field of view. The algorithm does not involve interactive steps. The method is rapid and effective, and thus applicable to industrial applications.

10 Claims, 6 Drawing Sheets

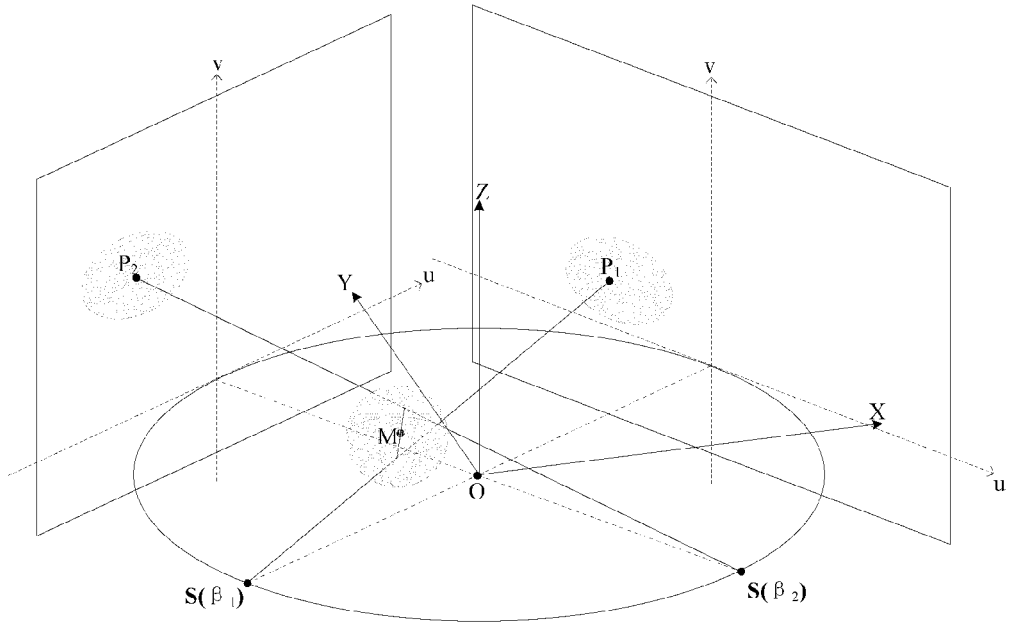

Fig. 8

S91: DETERMINE LOCATION OF A PARTICULAR OBJECT IN THE THREE-DIMENSIONAL SPACE BASED ON THE PROJECTION DATA

S92: PARTITION THE PROJECTION IMAGES OF ALL ANGLES WITH RESPECT TO OBJECTS BY USING THE COORDINATES OF CENTER OF GRAVITY OF THE PLURALITY OF PARTICULAR OBJECTS

S93: RECOVER PROJECTION DATA OF THE PLURALITY OF PARTICULAR OBJECTS FROM THE PROJECTION DATA THAT HAVE PARTITIONED THE PLURALITY OF OBJECTS THEREFROM

S94: PERFORM A CT RECONSTRUCTION ON THE RECOVERED PROJECTION DATA TO OBTAIN A CT IMAGE THAT DOES NOT CONTAIN THE PLURALITY OF PARTICULAR OBJECTS

Fig. 9

METHODS AND DEVICES FOR LOCATING OBJECT IN CT IMAGING

TECHNICAL FIELD

The embodiments of the present invention generally relate to Computed Tomography (CT), and more particularly, to methods and devices for locating an object in CT imaging.

BACKGROUND

Since Hounsfield invented the first CT machine in 1972, the CT technology brings out outstanding affect in medical diagnosis and industrial lossless detection. The CT technology now becomes one of the important detection means in various industries such as medicine, biology, aviation, national defense, etc. As the technology develops, the CT scanning and imaging improves increasingly, and the three-dimensional cone beam CT becomes the object of research and application. X-ray cone beam CT is applicable in various fields such as medical clinic, security inspection, lossless detection, etc. The CT becomes an indispensable detection means in the medical clinic.

The spiral CT is applied to the medical clinic since 1989. It gradually replaces the conventional CT technologies due to its prominent advantages. The advantage of the spiral CT over the conventional CT is that the spiral CT can collect projected data continuously without any interruption, and can obtain the three-dimensional body data of an object by means of a specially designed reconstruction algorithm, thereby the time required for CT scanning is reduced greatly, a Z-axis resolution of the reconstructed image can be provided, and the false track of movement can be reduced. The spiral CT is successful in the clinic application, and thus the detector used in the spiral CT develops from a single slice to 2 slices, 4 slices, 8 slices, 16 slices, and to 32 slices, 64 slices or even 128 slices. A spiral CT of 320 slices was released the first time by Toshiba Company in 2007. Another technology, i.e., a panel detector technology, improves as the spiral CT progresses. The multi-slice spiral CT uses an array of detectors composed of several independent detector modules, while the panel detector uses a one-piece scintillator of a large area with a large-scale array of light sensitive units, such as CCD, CMOS, TFT, etc., packaged at the back, where the X-ray intensity data is obtained after an analog to digital conversion. The progress of the panel detector technology brings out a new cone beam CT, i.e., CBCT. A CBCT system using the panel detector technology is capable of scanning a large region, such as 30 cm*30 cm, by rotating only one round and reconstructing a three-dimensional CT image within the field of view (FOV) of the scanning.

The CT technology also processes in the field of security inspection and industrial detection. For example, the CT used for security inspection which is based on the double energy mechanism is accepted and popularizes in the field of security inspection due to its good performance of differentiating substances. The industrial CT used in the industrial lossless detection field improves in respect to the spatial resolution, density resolution, etc.

It is also an important topic of research as how to accurately determine locations of interested objects (such as a metal object) during the process of CT image reconstruction.

SUMMARY

In view of one or more problems of the prior art, methods and devices for locating an object in CT imaging are provided.

According to embodiments of the invention, there is provided a method for locating a plurality of interested objects in CT imaging, including:

computing from projection data a first projection image at an observation direction perpendicular to a CT tomographic plane by means of a projection synthesis algorithm;

selecting two projection images, referred as a second projection image and a third projection image, from a cone beam projection perpendicular to the observation direction, the second projection image being substantially orthogonal to the third projection image;

determining locations of the plurality of interested objects in the first, second and third projection images; and computing locations of each of interested objects in the three-dimensional space based on the locations of the plurality of interested objects in the first, second and third projection images.

According to an embodiment, calculating the first projection image includes:

calculating a partial derivative of Radon data corresponding to the first projection image based on the projection data by using the relationship between the projection data and Radon transform values; and calculating the first projection image based on a filter back projection algorithm and the partial derivative of Radon data.

According to an embodiment, selecting two projection images includes:

selecting the second projection image and the third projection image based on the first projection image, so that the overlapping region of the plurality of interested objects in the second and third projection images are minimal.

According to an embodiment, selecting the second projection image and the third projection image based on the first projection image includes:

segmenting the first projection image to obtain a binary image containing only information on an interested region;

performing a forward projection of fan beams on the binary image to obtain a sonogram of fan beam projection, where a fan angle of the applied fan beam is equal to an open angle of a corresponding light source target point of a central slice of a cone beam system;

counting peaks by a peak founding algorithm for each column of the sinogram; and selecting two projection angles that are 90 degrees relative to each other from projection angles at which the count of peaks is equal to the number of interested objects in the first projection image, thereby determining the second projection image and the third projection image.

According to embodiments of the invention, determining locations of the plurality of interested objects in the first, second and third projection images includes:

partitioning the first projection image with respect to the respective interested objects and determining center of gravity of each of the interested objects in the first projection image; and partitioning the second and third projection images with respect to the respective interested objects and determining center of gravity of each of the interested objects in the second and third projection images.

According to embodiments of the invention, there is provided a device for locating a plurality of interested objects in CT imaging, including:

a computer configured to compute a first projection image at an observation direction perpendicular to a CT tomographic plane by means of a projection synthesis algorithm;

a selector configured to select two projection images, referred as a second projection image and a third projection image, from a cone beam projection perpendicular to the observation direction, the second projection image being substantially orthogonal to the third projection image;

a location determining component configured to determine locations of the plurality of interested objects in the first, second and third projection images; and a computer configured to compute locations of each of interested objects in the three-dimensional space based on the locations of the plurality of interested objects in the first, second and third projection images.

According to the embodiments, locations of interested objects can be determined from CT projection data.

BRIEF DESCRIPTION OF THE DRAWINGS

The invention will be described in details in conjunction with the accompanying drawings so as to better understand the invention, where

FIG. 8 explains the operation of selecting two orthogonal horizontal projection images from the top view;

FIG. 9 illustrates a flowchart of a method for cancelling artifact in CT imaging according to another embodiment of the invention.

DETAILED DESCRIPTION OF THE EMBODIMENTS

Figure 1:
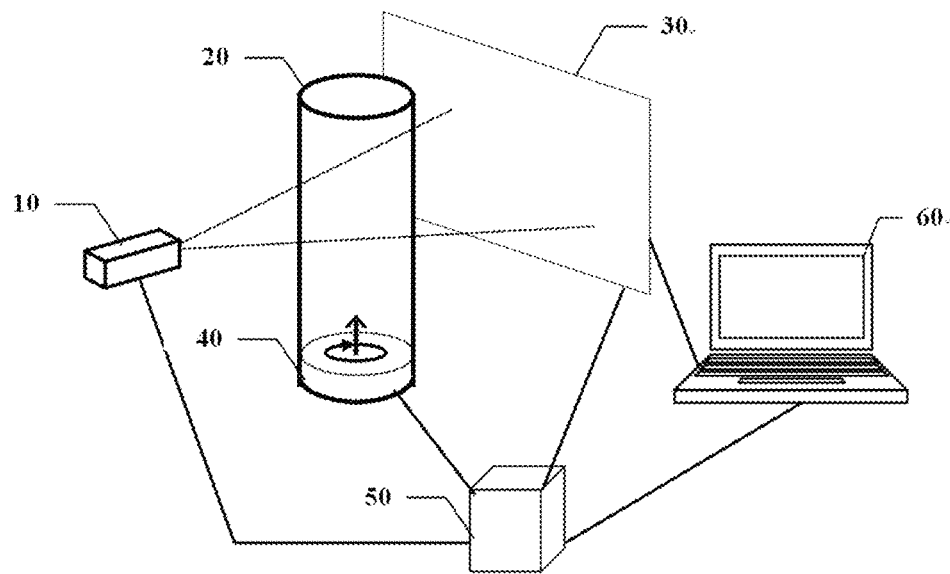
FIG. 1 is a structural diagram of a CT device according to an embodiment of the invention.

The particular embodiments of the invention are described below in details. It shall be noted that the embodiments herein are used for illustration only, but not limiting the invention. In the description below, a number of particular details are explained to provide a better understanding to the invention. However, it is apparent to those skilled in the art to the invention can be implemented without these particular details. In other examples, well known circuits, materials or methods are not described so as to not obscure the invention.

Throughout the specification, the reference to "one embodiment," "an embodiment," "one example" or "an example" means that the specific features, structures or properties described in conjunction with the embodiment or example are included in at least one embodiment of the present invention. Therefore, the phrases "in one embodiment," "in an embodiment," "in one example" or "in an example" occurred at various positions throughout the specification may not refer to one and the same embodiment or example. Furthermore, specific features, structures or properties may be combined into one or several embodiments or examples in any appropriate ways. Moreover, it should be understood by those skilled in the art that the drawings are provided herein for illustration purpose, and not necessarily drawn to scale. It should be understood that when it is referred that an "element" is "connected" or "coupled" to another element, it may be connected or coupled directly to the other element, or there may be an intermediate element. Otherwise, when it is referred that an element is "directly connected" or "directly coupled" to another element, there is no intermediate element.

According to some embodiments of the invention, a plurality of interested objects can be located in CT imaging. A first projection image at an observation direction perpendicular to a CT tomographic plane is computed from projection data by means of a projection synthesis algorithm. Two projection images (hereinafter referred as a second projection image and a third projection image) are selected from a cone beam projection perpendicular to the observation direction, where the second projection image is substantially orthogonal to the third projection image. Locations of the plurality of interested objects in the first, second and third projection images are determined. Locations of each of interested objects in the three-dimensional space are computed based on the locations of the plurality of interested objects in the first, second and third projection images.

According to other embodiments of the invention, the artifact in CT imaging can be cancelled. Locations of the plurality of particular objects in the three projections images that are substantially perpendicular to each other are calculated from the projection data, thereby the locations of the plurality of particular objects in the three-dimensional space can be determined. The projection images of all the projection angles are partitioned with respect to the objects by using the coordinates of the centers of gravity of the plurality of particular objects. Projection data of the plurality of particular objects are recovered by using the projection data where the plurality of particular objects are partitioned. A CT reconstruction is performed by using the recovered projection data, to obtain a CT image not containing the plurality of particular objects.

FIG. 1 is a structural diagram of a CT device according to an embodiment of the invention. As shown in FIG. 1, the CT device according to the embodiment includes a ray source 10 which is configured to emit an X ray for detection, such as an X ray machine; a carrier mechanism 40 which carries a to-be-detected object to rotate around the Z axis, and may lift and/or descend to cause the to-be-detected object to enter a detection region, so that the rays emitted from the ray source 10 permeate the to-be-detected object; a detection and collection unit 30 which includes a detector and a data collector that are integral, such as a plane detector, and is configured to detect rays transmitted the to-be-detected object to obtain an analog signal, and to transform the analog signal to a digital signal so as to output projection data of the to-be-detected object with respect to X rays; a controller 50 which is configured to control respective parts of the whole system to operate in synchronization; and a computer data processor 60 which is configured to process data collected by the data collector, process and reconstruct the data to output a result.

As shown in FIG. 1, the ray source 10 is placed at one side of the carrier mechanism 40 on which the to-be-detected object may be positioned, and the detection and collection unit 30 is placed at another side of the carrier mechanism 40. The detection and collection 30 includes a detector and a data collector, and may acquire projection data and/or multi-angle projection data of the to-be-detected object. The data collection includes a data amplifying and shaping circuit which works by a (current) integration way or a pulse (counting) way. The detection and collection unit 30 has a data output cable connected to the computer data processor 60, and stores the collected data in the computer data processor 60 according to a trigger instruction.

Moreover, the device may further includes a bucket-shaped object channel 20 which is made of metal and placed on the carrier mechanism 40, within which the to-be-detected object is placed.

Figure 2:
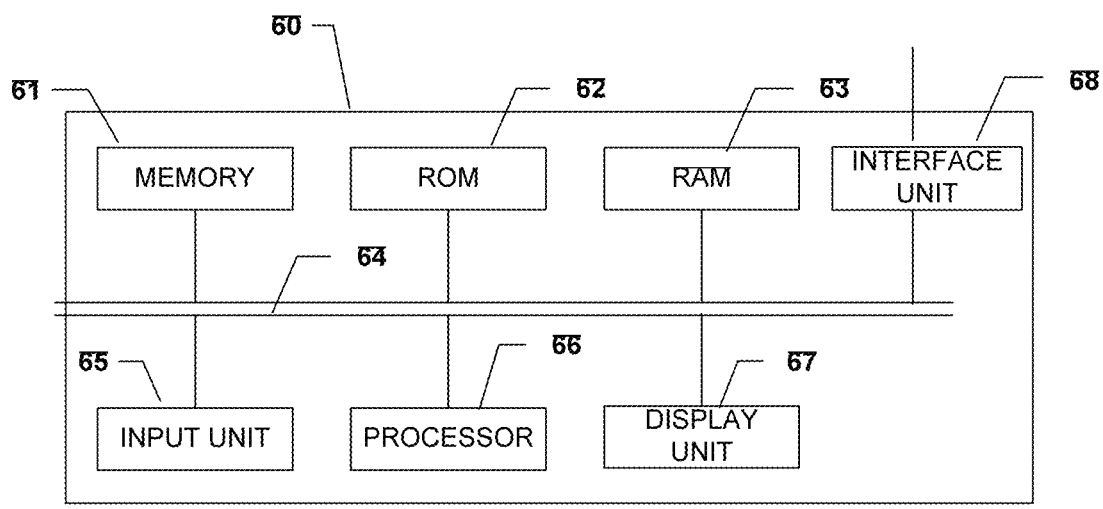
FIG. 2 illustrates a diagram of a computer data processor shown in FIG. 1.

FIG. 2 illustrates a diagram of the computer data processor 60 shown in FIG. 1. As shown in FIG. 2, the data collected by the data collector are stored in a memory 61 via an interface unit 68 and bus 64. A read only memory (ROM) 62 stores therein configuration information and programs of the computer data processor. A random access memory (RAM) 63 stores transitorily various data in the course of the operation of the processor 66. Moreover, the memory 61 also stores therein a computer program which is used for data processing. The internal but 64 connects the memory 61, ROM 62, RAM 63, input unit 65, processor 66, display unit 67 and interface unit 68.

When a user inputs an operation instruction via the input unit 65, for example a keyboard, a mouse and others, codes of the computer program instruct the processor 66 perform a predefined data processing algorithm. When the result of data processing has been obtained, it is displayed on the display unit 67, for example a LCD display, or it is outputted through a hard copy, such as printing.

Figure 3:
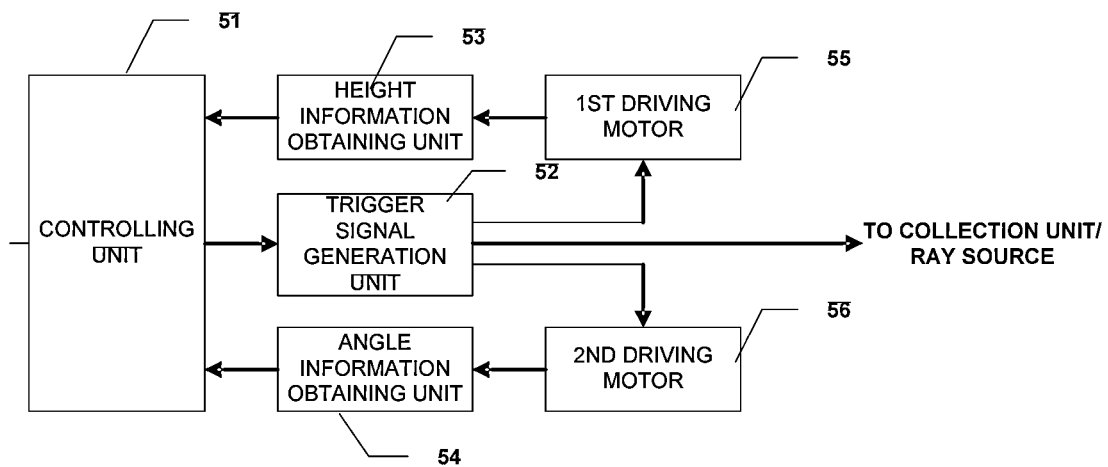
FIG. 3 illustrates a diagram of a controller according to a first embodiment of the invention.

FIG. 3 illustrates a diagram of a controller according to the embodiment of the invention. As shown in FIG. 3, controller 50 includes a controlling unit 51 which is configured to control the ray source 10, the carrier mechanism 40 and the detection and collection unit 30 based on an instruction from the computer 60; a trigger signal generation unit 52 which is configured to generate, under the control of the controlling unit, a trigger instruction that activates the ray source 10, detection and collection unit 30 and the carrier mechanism 40; a first driving motor 55 which is configured to drive the carrier mechanism 40 to lift or descend in accordance with the trigger instruction generated by the trigger signal generation unit 52 under the control of the controlling unit 51; a height information obtaining unit 53 which is configured to move along with the carrier mechanism 40, and feed height information of the carrier mechanism back to the controlling unit 51; a second driving motor 56 which is configured to drive the carrier mechanism 40 to rotate in accordance with the trigger instruction generated by the trigger signal generation unit 52 under the control of the controlling unit 51; an angle information obtaining unit 54 which is configured to obtain information on the rotation angle of the carrier mechanism 40 during rotation of the carrier mechanism 40 and feed it back to the controlling unit 51. According to the embodiment of the invention, the height information obtaining unit 53 and the angle information obtaining information 54 both are optical encoders that have anti-jamming property.

Figure 4:
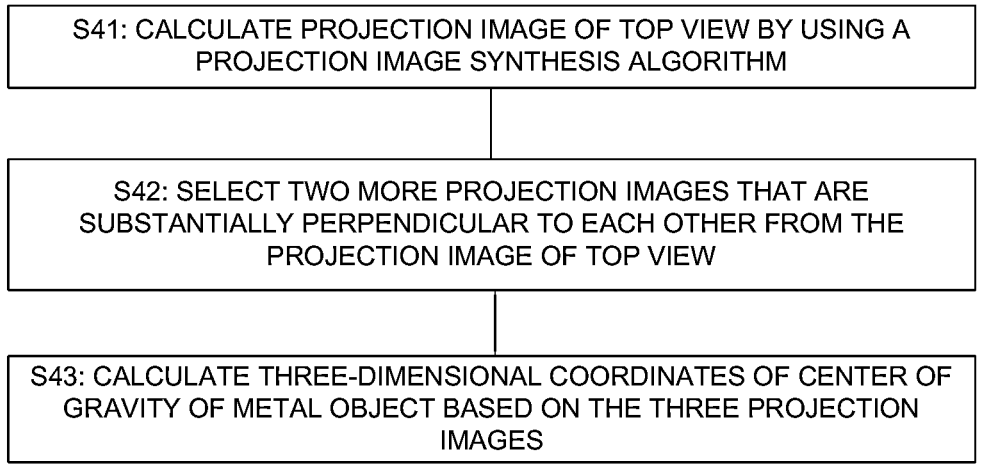
FIG. 4 illustrates a method for locating an object according to an embodiment of the invention.

Hereunder it is described in details a method for locating a particular object (interested object) in CT imaging based on three views. FIG. 4 is a diagram illustrating a method for locating an object according to an embodiment of the invention.

Figure 5:
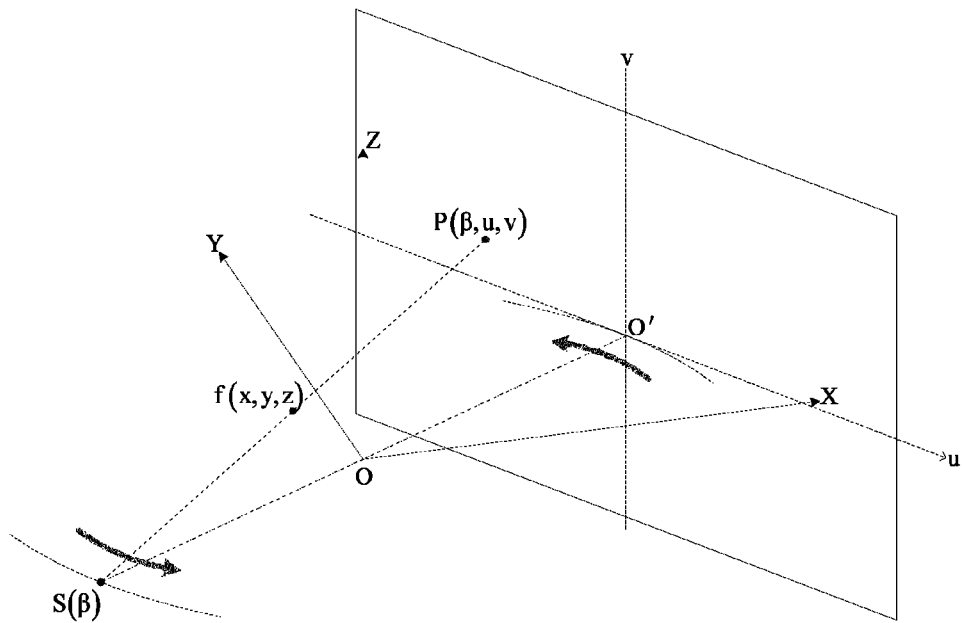
FIG. 5 is a diagram illustrating a CBCT system.

It is assumed that a CBCT system is as follows. A region to be reconstructed is expressed in a three-dimensional cartesian coordinate system Oxyz, where the origin O is the rotation center of the system. S(β) is the location of the cone beam ray source, where β is the value of the rotation angle of the system. A plane detector 30 is placed at one side of the rotation center and rotates in synchronization to the light source. The projection data on the detector is expressed in P(β,u,v), where u and v are cartesian coordinates on the plane detector. A diagram of the CBCT is shown in FIG. 5.

At step S41, a first projection image at an observation direction perpendicular to a CT tomographic plane is calculated from the projection data by means of a projection synthesis algorithm.

A parallel beam projection image of top view in the imaging field of view is calculated from the collected cone beam CT (CBCT) projection data. For example, a partial derivative of Radon data corresponding to the first projection image is calculated based on the projection data by using the relationship between the projection data and Radon transform values. For example, a partial derivative of Radon data corresponding to a top view (i.e., the first projection image in the example) may be calculated by equation (1):

$$\frac{\partial}{\partial u} R_f(s, \vec{m}) = \frac{1}{\cos^2\gamma} \int_{t_1}^{t_2} \frac{\partial}{\partial u}\left( \frac{SO}{SA(t)} \times P(\beta, u(s, \vec{m}), v(s, \vec{m}, t)) \right) dt \quad (1)$$

Figure 6:
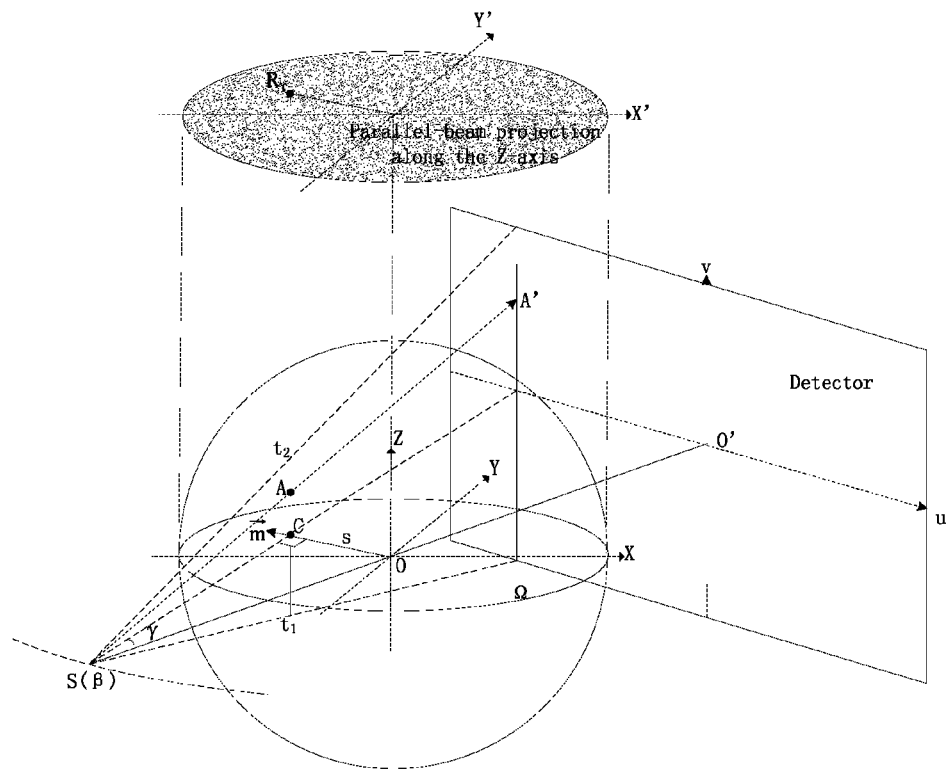
FIG. 6 is a diagram illustrating an algorithm of synthesizing projection data to obtain a parallel beam projection image of top view.

As shown in FIG. 6, point C is located at a center plane Ω, the length of OC corresponds to s in equation (1), $\vec{m}$ is a unit vector of the vector $\vec{OC}$, and γ represents ∠CSO. The integration is performed along the line $t_1 t_2$ that is perpendicular to the horizontal plane and passes point C.

The first projection image is then calculated based on a filter back projection algorithm and the partial derivative of Radon data. For example, the parallel beam projection image of top view is obtained by equation (2):

$$Pf(\vec{r}) = \frac{1}{2\pi} \int_0^\pi \left[ \frac{\partial Rf(s)}{\partial s} * h_H(s) \right]\bigg|_{s=\vec{r}\cdot\vec{m}} d\beta \quad (2)$$

where $h_H(s)$ is a Hilbert filtering, which is:

$$h_H(s) = \int_{-\infty}^{+\infty} (-i\cdot\text{sign}(\rho)) \cdot e^{2\pi i \rho s} d\rho \quad (3)$$

At step S42, two projection images, referred as a second projection image and a third projection image, are selected from a cone beam projection perpendicular to the observation direction, the second projection image being substantially orthogonal to the third projection image.

In the embodiment, the location of a metal block is represented by the three-dimensional coordinates of a certain metal anchor point (MAP) in the metal block. All the MAPs are located in the three-dimensional space based on projection images of three view-angles, where one of the projection images is that projection image of top view obtained in the last step, and the other two are selected from all the cone beam projection images. The parallel beam projection image of top view is used to assist the selection of the two horizontal cone beam projection images, so that the overlapping region of the metal blocks in the two projection images are minimal, and it is better to have the rotation angles of the two projection images be perpendicular to each other to reduce the calculation error.

Figure 7:
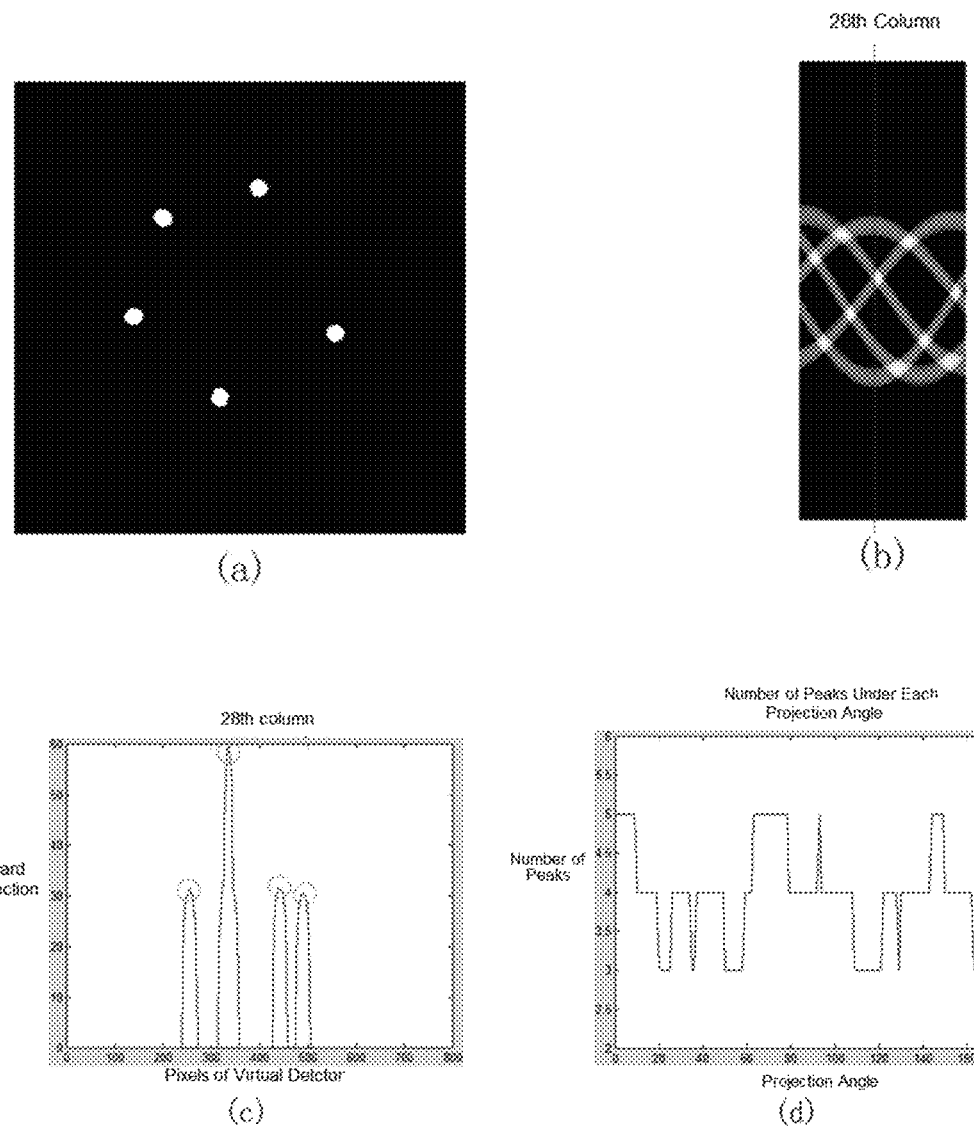
FIG. 7 illustrates a diagram where all the alternative MAPs are located.

FIG. 7 introduces a method of selecting a horizontal view angle image from a top view image by taking a set of real data as an example. The top view image is first segmented to obtain a binary image containing only information on the metal region. A forward projection of fan beams is performed on the binary image, to obtain a sonogram of fan beam projection, where the fan angle of the applied fan beam is equal to the open angle of a corresponding light source target point of a central slice of a cone beam system, so as to simulate the cone beam projection process from a top view. Peaks are counted by a peak founding algorithm for each column of the sinogram. Two projection angles, $angle_1$ and $angle_2$, that are substantially perpendicular to each other are selected from the projection angles at which the count of the peaks is equal to the number of metal blocks in the top view image by equation (4):

$$(angle_1, angle_2) = \arg\min \|angle_1 - angle_2| - 90°| \quad (4)$$

At step S43, locations of the plurality of interested objects in the first, second and third projection images are determined, and locations of each of interested objects in the three-dimensional space are calculated based on the locations of the plurality of interested objects in the first, second and third projection images.

For example, the selected two horizontal projection images are partitioned with respect to the metal regions and center of gravity of each of metal regions is calculated by equation (5):

$$\begin{cases} u_c(i) = \dfrac{\sum_{(u,v)\in M_i} P(u,v)\cdot u}{\sum_{(u,v)\in M_i} P(u,v)} \\ v_c(i) = \dfrac{\sum_{(u,v)\in M_i} P(u,v)\cdot v}{\sum_{(u,v)\in M_i} P(u,v)} \end{cases} \quad (5)$$

where $(u_c(i), v_c(i))$ is the coordinate of the center of gravity of the i-th metal region $M_i$.

In the three-dimensional space, the three images are used to locate all the MAPs. If the metal block is a convex geometrical body, a line connecting the light source and the center of gravity of the metal region will penetrate the metal block, and a crossing point of two known lines that penetrate one and the same metal block can be taken as the MAP of the metal block. As shown in FIG. 8, two lines generally do not intersect in a space in a practical situation. Thus, the least square solution of the two lines can be taken as the coordinate of the MAP, as illustrated by equation (6):

$$(x_m, y_m, z_m) = \arg\min(d^2(x,y,z,l_1) + d^2(x,y,z,l_2)) \quad (6)$$

where $d(x,y,z,l_1)$ and $d(x,y,z,l_2)$ represent the distances from $(x_m, y_m, z_m)$ to the two lines $l_1$ and $l_2$, respectively.

After $M(x_m, y_m, z_m)$ is calculated, it may be checked by using the third projection image to see whether $M(x_m, y_m, z_m)$ projects within the corresponding metal region. If yes, $M(x_m, y_m, z_m)$ may be recorded as the MAP.

The parallel beam projection image of top view is used to assist the selection of the horizontal projection images, to try to avoid overlapping of the metal blocks from occurring in the horizontal projection images. In the practical situation, it is complex. Here the practical case is discussed. It is assumed that there are m metal blocks in the field of view, the parallel beam projection image of top view contains $n_o$ metal regions, and the two horizontal projection images contain $n_1$ and $n_2$ metal regions, respectively, where it is assumed that $n_1 \geq n_2$ without loss of generality. There are three cases to be discussed.

(1) $m = n_o = n_1 = n_2$, which means that there is no overlapping of metal blocks in the three selected images. Accordingly, the centers of gravity of all metal regions calculated by equation (5) are accurate. We may take any two of the three images, and use equation (6) to calculate the possible coordinates of MAP, and use the left image to filter out the wrong options.

(2) $m = n_o = n_1 > n_2$ or $m = n_1 = n_2 > n_o$, which means that there are two images of the three image in which metal blocks are completely separate and do not overlap. We may take the two images where the metal blocks do not overlap, and use equation (6) to calculate the possible coordinates of MAP, and use the left image to filter out the wrong options.

(3) $m = n_o > n_1 \geq n_2$ or $m = n_1 > n_0 \cap n_1 > n_2$, which means that there is only one image in which metal blocks do not overlap. If $m > \max(n_o, n_1)$ stands, all the three image contain a region where the metal blocks overlap with each other. In these two cases, the present method cannot be applied to calculate the coordinates of MAP.

By the above process, the location of an interested object can be determined from CT projection data.

Furthermore, with respect to the problem of metal artifact that generally exists in CT projection data, another embodiment of the invention provides a method for correcting CT metal artifact based on three views, which can cancel the metal artifacts in CT imaging by using a projection synthesis technique and based on a three-views-based multiple-object three-dimensional coordinate locating technique. The method according to the embodiment of the invention is a correction method that pre-processes projection, and does not need CT pre-reconstruction. The algorithm is simple with a fast calculation speed, and thus can meet the requirement on reconstruction speed of industrial applications well.

In the method according to the embodiment, it can rapidly cancel the metal artifact in the reconstructed image even if there are a plurality of metal objects in the field of view. The outstanding advantage is that the image is not subject to reconstruction, and the algorithm does not involve iterative steps, while only three projection images of (substantially) perpendicular view angels are used to locate the metal blocks. Thus, the projection data can be recovered rapidly and accurately.

FIG. 9 illustrates a flowchart of a method for cancelling artifact in CT imaging according to another embodiment of the invention. As shown in FIG. 9, at step S91, locations of the plurality of particular objects in three projection images that are substantially perpendicular to each other are calculated from the projection to data, to determine the locations of the plurality of particular objects in the three-dimensional space.

According to another embodiment, the method of calculating locations of the plurality of particular objects in three projection images that are substantially perpendicular to each other to determine the locations of the plurality of particular objects in the three-dimensional space is as follows.

1) A parallel beam projection image of top view is calculated from the projection data by a projection synthesis algorithm at the first. By taking the location relationship of the metal regions in the projection image of top view into account, two projection images are selected from all the horizontal cone beam projection images, in which the metal blocks overlap to the least extent, and the difference of the rotation angles of the two horizontal projection images approximates 90 degrees as much as possible, to ensure the accuracy of the subsequent calculations.

2) The selected three projection images are partitioned with respect to metal regions. The locations of the metal blocks in the three-dimensional space are calculated based on the locations of the metal blocks in the three projection images, where the three-dimensional coordinate of center of gravity of each of the metal blocks is marked as the metal anchor point (MAP) of the metal block. In the practice, it is inevitable that the metal blocks in the selected projection images overlap. It is validated that the algorithm can accurately locate the MAPs of all the metal blocks as long as at least two of the three images do not contain overlapping metal regions.

At step S92, the projection images are partitioned with respect to the objects by using the coordinates of the centers of gravity of the plurality of particular objects.

At step S93, the projection data of the plurality of particular objects are recovered by using the projection data where the plurality of particular objects are partitioned.

At step S94, a CT reconstruction is performed by using the recovered projection data, to obtain a CT image not containing the plurality of particular objects.

For example, the MAP is projected on the plane of the detector in various angles, to obtain projection points which are called metal seed points (MSPs). From the MSPs, projection images of each of the angles are pre-processed, to partition all the metal regions in the projection images by taking the MSPs as the seed points. After all the metal regions in the projection images are partitioned, the projection data at the partitioned metal regions are recovered (using a normal interpolation method is possible). A CT image not containing the metal blocks can be reconstructed from the recovered projection data by using an existing CT reconstruction algorithm.

For example, after all the MAPs are located in the three-dimensional space, the projection of the MAP on the plane detector in each of projection angles is calculated, and recorded as meta seed points (MSPs). Because the MAP is determined to be located at inside of the metal block in the three-dimensional space, MSP definitely locates at inside of the metal projection region in the projection image. Therefore, all the metal projection regions may be partitioned in the projection images by using a well established region growing algorithm.

After the metal regions in the projection images have been marked, the metal projection regions are recovered by using a bilinear interpolation algorithm. The algorithm is expressed as equation (7):

$$I = \frac{\frac{\left(\begin{array}{c} d_{up} \times I_{down} + \\ d_{down} \times I_{up} \end{array}\right)}{(d_{up} + d_{down})} \times (d_{left} + d_{right}) + \frac{\left(\begin{array}{c} d_{left} \times I_{right} + \\ d_{right} \times I_{left} \end{array}\right)}{(d_{left} + d_{right})} \times (d_{up} + d_{down})}{d_{up} + d_{down} + d_{left} + d_{right}} \quad (7)$$

where I is the recovered data to be filled in the corresponding pixel, $d_{up}$, $d_{down}$, $d_{left}$ and $d_{right}$ are the distances from the pixel to the edges of the metal region, $I_{up}$, $I_{down}$, $I_{left}$ and $I_{right}$ are the gray values of the images at the corresponding edges.

After the projection data have been pre-processed by the above method, a new CT image that does not contain the metal blocks can be re-constructed by using an existing CT method (for example, circular orbit FDK algorithm, spiral orbit FDK algorithm, etc.).

The above theory and method are validated in a real system. FIG. 10(a) illustrates a CBCT system to be used. The plane detector has a size of 243.84 mm×195.07 mm, where each pixel has a size of 0.127 mm×0.127 mm, which means that the array includes 1920×1536 pixels. The X ray source is located in opposition to the detector, with a voltage of 120 keV and a current of 1.7 mA. A rotation platform is located between the detector and the light source. The target point of the light source is 750 mm away from the center of the rotation platform, and 1050 mm away from the center of the detector. 360 projections evenly distributed in the 360° range are collected for each scanning. A model is established to explain the algorithm (as shown in FIG. 10(b)). A plastic flask is fixed at a plastic beaker, and several metal balls are fixed at outside of the flask. In order to simulate a medical application, the beaker and the flask both are filled with water during the scanning process.

Figure 10:
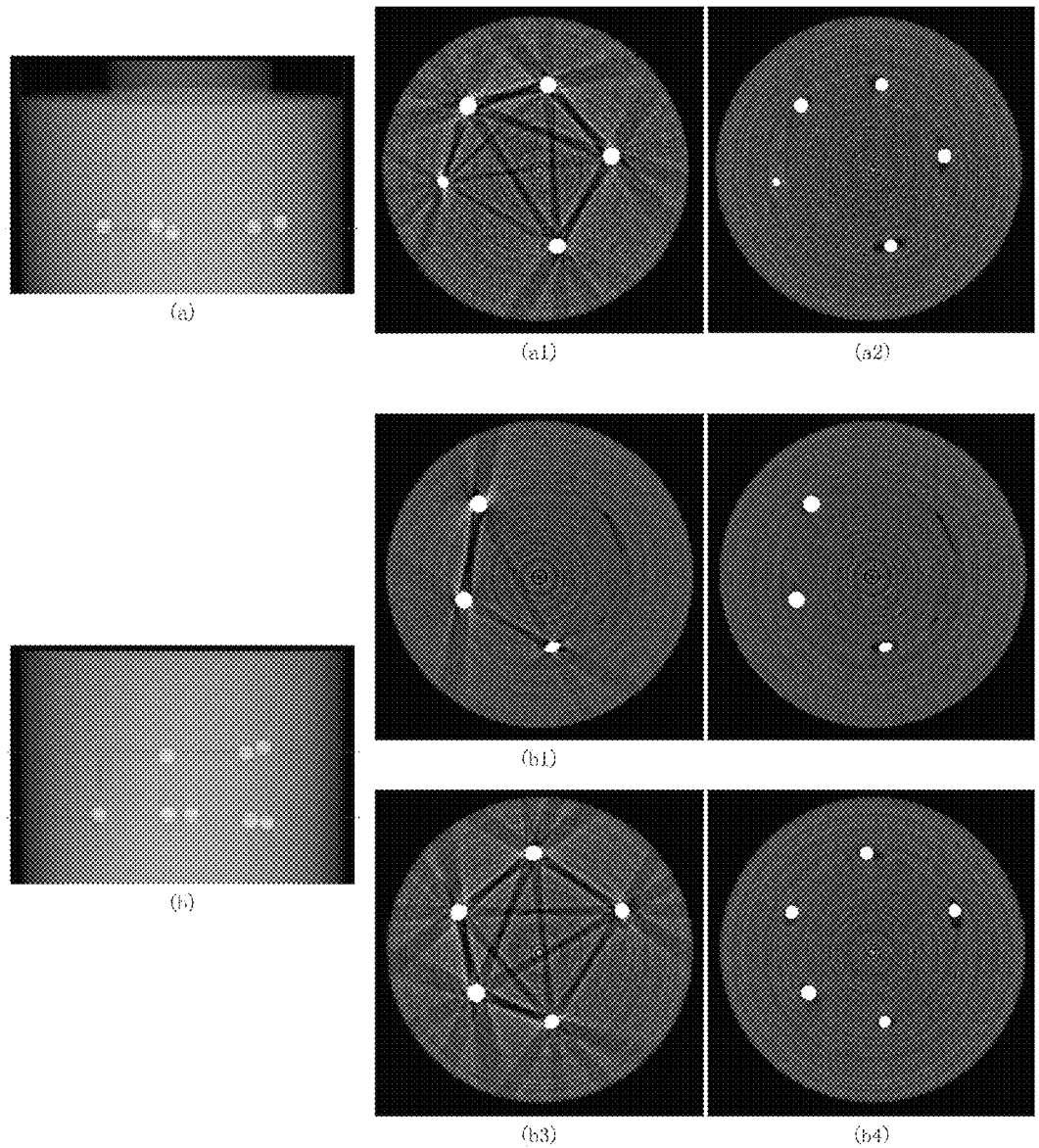
FIG. 10 illustrates the result of artifact cancelling.

The simulation result is shown in FIG. 10. The metal balls are fixed at outside of the flask by two different ways, so as to check whether the different location relationship would affect the location algorithm. FIGS. 10(a1), 10(b1) and 10(b3) show the CT images that have not been processed, and FIGS. 10(a2), 10(b2) and 10(b4) show the CT images to which the method according to the present invention has been applied to correct metal artifact. It can be seen that the strip artifact between the metal blocks and the artifact adjacent to the metal blocks can be effectively cancelled by the metal artifact correcting method according to the present invention.

The artifact correcting method starts from the image processing method in the projection domain, and can rapidly and effectively address the problem of metal artifact that may occur when a plurality of metal blocks exist. Furthermore, the method does not need iterative operations, and can easily be used in a practical project.

The foregoing detailed description has set forth various embodiments of the method of locating an object and/or the method of correcting artifact via the use of block diagrams, flowcharts, and/or examples. Insofar as such block diagrams, flowcharts, and/or examples contain one or more functions and/or operations, it will be understood by those skilled in the art that each function and/or operation within such block diagrams, flowcharts, or examples may be implemented, individually and/or collectively, by a wide range of hardware, software, firmware, or virtually any combination thereof. In one embodiment, several portions of the subject matter described herein may be implemented via Application Specific Integrated Circuits (ASICs), Field Programmable Gate Arrays (FPGAs), digital signal processors (DSPs), or other integrated formats. However, those skilled in the art will recognize that some aspects of the embodiments disclosed herein, in whole or in part, may be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of those skilled in the art in light of this disclosure. In addition, those skilled in the art will appreciate that the mechanisms of the subject matter described herein are capable of being distributed as a program product in a variety of forms, and that an illustrative embodiment of the subject matter described herein applies regardless of the particular type of signal bearing medium used to actually carry out the distribution. Examples of a signal bearing medium include, but are not limited to, the following: a recordable type medium such as a floppy disk, a hard disk drive, a Compact Disc (CD), a Digital Versatile Disk (DVD), a digital tape, a computer memory, etc.; and a transmission type medium such as a digital and/or an analog communication medium (e.g., a fiber optic cable, a waveguide, a wired communications link, a wireless communication link, etc.).

While the present invention has been described with reference to several typical embodiments, it is apparent to those skilled in the art that the terms are used for illustration and explanation purpose and not for limitation. The present invention may be practiced in various forms without departing from the esprit or essence of the invention. It should be understood that the embodiments are not limited to any of the foregoing details, and shall be interpreted broadly within the esprit and scope as defined by the following claims. Therefore, Modifications and alternatives falling within the scope of the claims and equivalents thereof are to be encompassed by the scope of the present invention which is defined by the claims as attached.

What is claimed is:

1. A method for locating a plurality of interested objects in Computed Tomography (CT) imaging, comprising:
    computing from projection data a first projection image at an observation direction perpendicular to a CT tomographic plane by means of a projection synthesis algorithm;
    selecting two projection images, referred as a second projection image and a third projection image, from a cone beam projection perpendicular to the observation direction, the second projection image being substantially orthogonal to the third projection image;
    determining locations of the plurality of interested objects in the first, second and third projection images; and
    computing locations of each of interested objects in the three-dimensional space based on the locations of the plurality of interested objects in the first, second and third projection images.

2. The method according to claim 1, wherein calculating the first projection image comprises:
    calculating a partial derivative of Radon data corresponding to the first projection image based on the projection data by using the relationship between the projection data and Radon transform values; and
    calculating the first projection image based on a filter back projection algorithm and the partial derivative of Radon data.

3. The method according to claim 1, wherein selecting two projection images comprises:
    selecting the second projection image and the third projection image based on the first projection image, so that the overlapping region of the plurality of interested objects in the second and third projection images are minimal.

4. The method according to claim 3, wherein selecting the second projection image and the third projection image based on the first projection image comprises:
    segmenting the first projection image to obtain a binary image containing only information on an interested region;
    performing a forward projection of fan beams on the binary image to obtain a sonogram of fan beam projection, where a fan angle of the applied fan beam is equal to an open angle of a corresponding light source target point of a central slice of a cone beam system;
    counting peaks by a peak founding algorithm for each column of the sinogram; and
    selecting two projection angles that are 90 degrees relative to each other from projection angles at which the count of peaks is equal to the number of interested objects in the first projection image, thereby determining the second projection image and the third projection image.

5. The method according to claim 1, wherein determining locations of the is plurality of interested objects in the first, second and third projection images comprises:
    partitioning the first projection image with respect to the respective interested objects and determining center of gravity of each of the interested objects in the first projection image; and
    partitioning the second and third projection images with respect to the respective interested objects and determining center of gravity of each of the interested objects in the second and third projection images.

6. A device for locating a plurality of interested objects in Computed Tomography (CT) imaging, comprising:
    a computer configured to compute a first projection image at an observation direction perpendicular to a CT tomographic plane by means of a projection synthesis algorithm;
    a selector configured to select two projection images, referred as a second projection image and a third projection image, from a cone beam projection perpendicular to the observation direction, the second projection image being substantially orthogonal to the third projection image;
    a location determining component configured to determine locations of the plurality of interested objects in the first, second and third projection images; and
    a computer configured to compute locations of each of interested objects in the three-dimensional space based on the locations of the plurality of interested objects in the first, second and third projection images.

7. The device according to claim 6, wherein means for calculating the first projection image comprises:
    a calculator configured to calculate a partial derivative of Radon data corresponding to the first projection image based on the projection data by using the relationship between the projection data and Radon transform values; and
    a calculator configured to calculate the first projection image based on a filter back projection algorithm and the partial derivative of Radon data.

8. The device according to claim 6, wherein means for selecting two projection images comprises:
    a selector configured to select the second projection image and the third projection image based on the first projection image, so that the overlapping region of the plurality of interested objects in the second and third projection images are minimal.

9. The device according to claim 8, wherein means for selecting the second projection image and the third projection image based on the first projection image comprises:
    a segmenter configured to segment the first projection image to obtain a binary image containing only information on an interested region;
    a projector configured to perform a forward projection of fan beams on the binary image to obtain a sonogram of fan beam projection, where a fan angle of the applied fan beam is equal to an open angle of a corresponding light source target point of a central slice of a cone beam system;
    a counter configured to count peaks by a peak founding algorithm for each column of the sinogram; and
    a selector configured to select two projection angles that are 90 degrees relative to each other from projection angles at which the count of peaks is equal to the number of interested objects in the first projection image, thereby determining the second projection image and the third projection image.

10. The device according to claim 6, wherein the location determining component configured to determine locations of the plurality of interested objects in the first, second and third projection images comprises:
    a first partitioner configured to partition the first projection image with respect to the respective interested objects and determining center of gravity of each of the interested objects in the first projection image; and a second partitioner configured to partition the second and third projection images with respect to the respective interested objects and determining center of gravity of each of the interested objects in the second and third projection images.

\* \* \* \* \*